United States Patent [19]

Kano et al.

[11] Patent Number: 4,703,059
[45] Date of Patent: Oct. 27, 1987

[54] TRIS(BETA,BETA-DIMETHYLPHENETHYL) TIN COMPOUNDS

[75] Inventors: Toshio Kano; Masamichi Knodo, both of Sagamihara; Tatsufumi Ikeda, Nagano; Chiharu Morikawa, Suzaka, all of Japan

[73] Assignee: Yashima Chemical Industrial Co., Ltd., Tokyo, Japan

[21] Appl. No.: 776,027

[22] Filed: Sep. 13, 1985

[30] Foreign Application Priority Data

Sep. 18, 1984 [JP] Japan ................................ 59-193975

[51] Int. Cl.$^4$ ...................... A01N 55/04; A61K 31/32
[52] U.S. Cl. ........................................ 514/493; 556/94
[58] Field of Search ........................... 556/94; 514/493

[56] References Cited

U.S. PATENT DOCUMENTS

| | | | |
|---|---|---|---|
| 3,657,451 | 4/1972 | Horne | 556/94 X |
| 3,703,588 | 11/1972 | Saito et al. | 556/94 X |
| 3,824,187 | 7/1974 | Gorsich | 556/88 X |
| 4,058,545 | 11/1977 | Gitlitz | 556/94 X |
| 4,185,094 | 1/1980 | Crump | 556/94 X |
| 4,222,950 | 9/1980 | Gitlitz | 556/94 X |
| 4,301,173 | 11/1981 | Imazaki et al. | 556/94 X |

OTHER PUBLICATIONS

Chemical Abstracts 64 5131h (1966).

Primary Examiner—Helen M. S. Sneed
Attorney, Agent, or Firm—Wenderoth, Lind & Ponack

[57] ABSTRACT

A compound represented by the formula

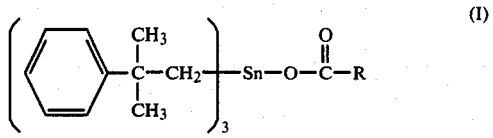

wherein R represents an alkyl group having 7 to 11 carbon atoms, a phenyl group which may be substituted by a lower alkyl group or a halogen atom, or a group of the formula

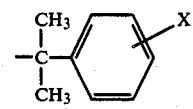

in which X represents a hydrogen or halogen atom. This compound can be prepared by reacting a compound represented by the formula

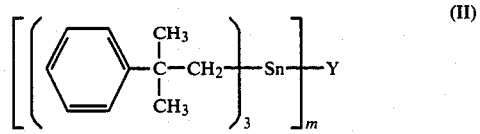

wherein m is an integer of 1 to 2, and Y represents a chlorine atom when m is 1 and —O— when m is 2, with a compound represented by the following formula

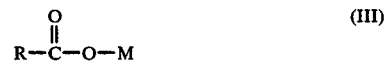

wherein M represents a hydrogen or alkali metal atom; and is useful as a miticide.

6 Claims, No Drawings

TRIS(BETA,BETA-DIMETHYLPHENETHYL) TIN COMPOUNDS

This invention relates to novel tris($\beta,\beta$-dimethylphenethyl) tin compounds, and more specifically to compounds represented by the following formula

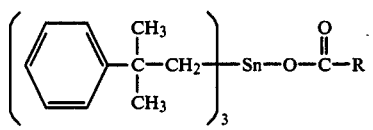

(I)

wherein R represents an alkyl group having 7 to 11 carbon atoms, a phenyl group which may be substituted by a lower alkyl group or a halogen atom, or a group of the formula

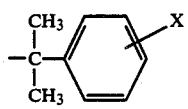

in which X represents a hydrogen or halogen atom, a process for producing these compounds and the use of these compounds as an active ingredient of a miticide.

Mites parasitic on plants grow and propagate within a short period of time, and do enormous damage to agricultural and horticultural produce. Organophosphorus miticides and organochlorine miticides are mainly used now to control mites. But because of their repeated application, mites have acquired resistance to these miticides, and are difficult to control with these chemicals. It is desired therefore to develop new miticides.

To meet such a desire, U.S. Pat. No. 3,657,451 disclosed a miticidal composition comprising a series of organotin compound including compounds of the following formula:

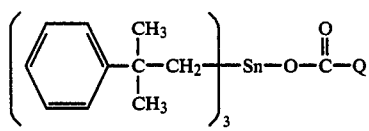

(A)

Q = C$_1$–C$_4$ alkyl

The present iventors synthesized many organotin compounds, and studied their biological activity. Consequently, they have found that the aforesaid compounds of formula (I) show excellent miticidal activity which is much higher than that of the known compounds of formula (A) without causing phytotoxicity to plants.

The compounds of formula (I) in accordance with this invention are novel compounds not described in the literature. They exhibit an excellent control effect on a broad range of noxious mites which are parasitic on various plants and do damage to the plants. They include, for example, *Panonychus citri, Panonychus ulmi, Tetranychus kanzawai, Tetranychus urticae, Tetranychus cinnabarinus, Aculops pelekassi,* and *Tetranychus viennensis.* Moreover, these compounds cause no phytotoxicity to useful crops.

The term "lower", as used herein to qualify a group or a compound means that the group or compound so qualified has not more than 6, preferably not more than 4, carbon atoms.

The term "alkyl group", as used herein, denotes a linear or branched saturated aliphatic hydrocarbon group. Specific examples of the alkyl group having 7 to 11 carbon atoms include heptyl, octyl, nonyl, decyl and undecyl groups. The lower alkyl group includes methyl, ethyl, n-propyl, isopropyl, n-butyl, isobutyl, sec-butyl and tert-butyl groups.

The term "halogen atom", as used herein, includes fluorine, chlorine, bromine and idoine atoms.

The following specific examples of the compound of formula (I) provided by this invention can be cited in addition to those given in Synthesis Examples and Table 1.

(1) tris($\beta,\beta$-dimethylphenethyl)tin undecylate,
(2) tris($\beta,\beta$-dimethylphenethyl)tin 4-ethylcaproate,
(3) tris($\beta,\beta$-dimethylphenethyl)tin 3-methylcaprylate
(4) tris($\beta,\beta$-dimethylphenethyl)tin 3,3-dimethyl-5-methylcaproate,
(5) tris($\beta,\beta$-dimethylphenethyl)tin p-methylbenzoate,
(6) tris($\beta,\beta$-dimethylphenethyl)tin p-n-butylbenzoate,
(7) tris($\beta,\beta$-dimethylphenethyl)tin p-iodobenzoate,
(8) tris($\beta,\beta$-dimethylphenethyl)tin p-fluorobenzoate,
(9) tris($\beta,\beta$-dimethylphenethyl)tin $\alpha,\alpha$-dimethylphenylacetate,
(10) tris($\beta,\beta$-dimethylphenethyl)tin $\alpha,\alpha$-dimethyl-p-fluorophenylacetate.

In view of miticidal activity, tris($\beta,\beta$-dimethylphenethyl)tin laurate corresponding to a compound of formula (I) in which R is an alkyl group having 11 carbon atoms (—C$_{11}$H$_{23}$) is particularly preferred among the compounds of formula (I) used in this invention.

The compounds of formula (I) in accordance with this invention can be produced, for example, by reacting a compound represented by the following formula

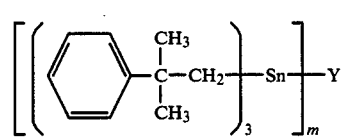

(II)

wherein m is an integer of 1 to 2, and Y represents a chlorine atom when m is 1 and —O— when m is 2, with a compound represented by the following formula

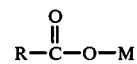

(III)

wherein M represents a hydrogen atom or an alkali metal atom such as sodium or potassium, and R is as defined above.

When a compound of formula (II) in which Y is —O— (m=2) is used as the starting material in the reaction of the compound of formula (II) with the compound of formula (III), M in the compound of formula (III) is desirably a hydrogen atom. When a compound of formula (II) in which Y represents a chlorine atom (m=1) is used as the starting material, M in the compound of formula (III) is desirably an alkali metal atom.

The above reaction is carried out usually in a suitable solvent. The solvent may be selected according to the starting materials used. For example, when the compound of formula (II) in which Y is an oxygen atom is to be reacted with the compound of formula (III) in which M is a hydrogen atom, the solvent is preferably a hydrocarbon such as benzene, toluene, xylene or n-heptane. In the reaction of the compound of (II) in which Y is a chlorine atom with the compound of formula (III) in which M is an alkali metal atom, the solvent is preferably a hydrophilic organic solvent, for example an alcohol such as ethanol or isopropanol or a ketone such as acetone.

The reaction temperature is generally about 50° C. to the refluxing temperature of the reaction mixture when the compound of formula (II) in which Y is —O— is reacted with the compound of formula (III) in which M is a hydrogen atom. Advantageously, the reaction is carried out within the above temperature range preferably using a solvent having a boiling point of at least 30° C. while removing water formed by the reaction out of the reaction system.

On the other hand, the reaction of the compound of formula (II) in which Y is a chlorine atom with the compound of formula (III) in which M is an alkali metal is carried out generally at a temperature of about 50° C. to the refluxing temperature of the reaction mixture, preferably from 30° to 80° C.

The proportion of the compound of formula (III) relative to the compound of formula (II) is not critical, and can be varied over a wide range depending upon the types of these compounds, for example. Generally, the suitable proportion of the compounds of formula (III) is 0.8 to 2.5 moles, preferably 1.0 to 2.0 moles per mole of the compound of formula (II).

The compound of formula (I) formed by the reaction described above can be isolated and purified by methods known per se such as column chromatography and recrystallization.

The starting compound of formula (II) in which Y is —O— used in the above method can be produced easily by, for example, reacting tris($\beta,\beta$-dimethylphenethyl)-tin chloride with an alkali metal compound such as sodium hydroxide and potassium hydroxide, or ammonium hydroxide in the aforesaid hydrophilic organic solvent at a temperature of about 50° to about 100° C.

The compounds of formula (I) show excellent combatting activity against mites parasitic on plants. The present invention, therefore, provides a miticide comprising the compound of formula (I) as an active ingredient.

As a miticide, the compound of formula (I) is generally formulated into a solid or liquid miticidal composition together with an agriculturally acceptable carrier or diluent. Examples of the carrier or diluent include solid carriers or diluents such as clay, talc, bentonite, diatomaceous earth and kaolin; and liquid carriers or diluent such as alcohols (e.g. methanol, propanol, or ethylene gycol), aromatic hydrocarbons (e.g. benzene, toluene or xylene), ketones (e.g. acetone, methyl ethyl ketone or methyl isobutyl ketone), esters (e.g. ethyl acetate), and amides (e.g. dimethylformamide or dimethylacetamide).

For various purposes such as the improvement of the properties of the miticidal composition or the increasing of its biological effect, the miticidal composition of this invention may further contain an emulsifier, a dispersant, a wetting agent, a sticker, a stabilizer, etc. in amounts commonly used.

Specific examples of the emulsifier are polyoxyalkylene alkyl ethers, polyoxyalkylene alkylaryl ethers, polyoxyalkylene sorbitan fatty acid esters, and alkylbenzenesulfonic acid salts.

Specific examples of the disprsant are alkylsulfuric acid ester salts, naphthalenesulfonic acid/formaldehyde condensate, polyoxyalkylene alkyl ether sulfuric acid ester salts, alkyl phosphoric acid ester salts and ligninsulfonic acid salts.

Specific examples of the wetting agent are polyoxyalkylene alkyl ethers, polyoxyalkylene alkylaryl ethers, dialkylsulfosuccinic acid esters salts, and polyoxyalkylene sorbitan fatty acid esters.

Specific examples of the sticker are polyvinyl alcohol, polyethylene glycol, carboxymethyl cellulose sodium salt and sodium alginate.

Specific examples of the stabilizer are isopropyl phosphate (PAP), polyoxyalkylene alkyl aryl phosphoric acid ester salts, phenyl glycidyl ether and epoxidized soybean oil.

The miticidal composition may further contain other biologically active substances commonly used, for example other miticides such as 4-chloro-$\alpha$-(4-chlorophenyl)-$\alpha$-(trichloromethyl)benzenemethanol (Dicofol) and tricyclohexylhydroxystannane (Cyhexatin), insecticides such as O,O-dimethyl O-(3-methyl-4-nitrophenyl)phosphorothiooate (Fenitrothion), O,O-diethyl O-[6-methyl-2-(1-methylethyl)-4-pyrimidinyl]phosphorothioate (Diazinon) and 1-naphthalenyl methylcarbamate (NAC), and fungicides such as D-3-O-[2-amino-4-[(1-carboxyiminomethyl)amino]-2,3,4,6-tetradeoxy-$\alpha$-D-arabino-hexopyranosyl]-D-chiro-inositol (Kasugamycin), 5-[(2-amino-5-O-(aminocarbonyl)2-deoxy-L-xylonyl]amino]-1,5-dideoxy-1-[3,4-dihydro-5-(hydroxymethyl)-2,4-dioxo-1(2H)-pyrimidinyl]-$\beta$-D-allofuranuroinic acid (Polyoxin) and [[1,2-ethanediyl bis[carbamodithioate]](2-)] zinc complex (Zineb].

The miticidal composition of this invention together with the aforesaid carriers or diluents and other additives may be formulated into various forms such as a wettable powder, an emulsifiable concentrate, a dust, a fine dust, etc. The content of the compound of formula (I) in the formulated composition is not critical and can be varied over a wide range according to the form of the composition, etc. Generally, it is within the range of 0.1 to 90% by weight based on the total weight of the composition. More specifically, it is generally 10 to 70% by weight, preferably 20 to 50% by weight, for wettable powders and emulsifiable concentrates. In application, they may be conveniently diluted so that the concentration of the compound of formula (I) is usually 0.005 to 0.1% by weight, preferably about 0.05% by weight. For dusts, the suitable content of the compound of formula (I) is generally 0.5 to 10% by weight, preferably 2 to 5% by weight, based on the total weight of the composition. With fine dusts, its content is generally 5 to 40% by weight, preferably 10 to 20% by weight based on the total weight of the composition.

Mites noxious to plants can be combatted by applying the miticidal composition of this invention directly to the mites or to their habitat or the locus where they occur. Its dosage is not critical, and can be varied according to the form of the composition, the state of growth of the mites, the extent of damage to plants, etc. Generally, the composition is applied at a rate of 15 to 1,000 g, preferably 30 to B 500 g, per 10 ares, as the active ingredient. For example, the wettable powder or emulsifiable concentrate is suitably applied at a rate of 300 to 600 liters/10 ares in a diluted form containing 0.005 to 0.1% by weight of the compound of formula (I). The dust and fine dust are preferably applied at a rate of 3 to 4 kg/10 ares and 300 to 500 g/10 ares, respectively.

The following examples illustrate the present invention more specifically.

SYNTHESIS EXAMPLE 1

(A) Tris($\beta,\beta$-dimethylphenethyl)tin chloride (55.6 g) was added to 200 ml of isopropanol, and the mixture was stirred at 50° C. To the resulting solution was added dropwise 40 g of a 12% aqueous solution of sodium hydroxide over 50 minutes. After the addition, the solution was further stirred at 50° C. for 60 minutes to complete the reaction. The reaction mixture was then filtered, and the residue was washed and dried to give 51.0 g of bis[tris($\beta,\beta$-dimethylphenethyl)tin] oxide as a white powder.

(B) To 120 g of toluene were added 26.6 g of bis[tris($\beta,\beta$-dimethylphenethyl)tin] oxide and 10.1 g of lauric acid. With stirring, the mixture was heated at the refluxing temperature to perform dehydration reaction. The water formed by the reaction was successively removed out of the reaction system. After confirming that the distillation of the resulting water was terminated, toluene was distilled off. As a result, 34.5 g (yield 96.4%) of tris(2,2-dimethylphenethyl)tin laurate was obtained as a slightly pale yellow viscous syrup.

Tin content: 16.1% (theory: 16.4%), Refractive index: $n_D^{25}$ 1.5387.

SYNTHESIS EXAMPLE 2

To 100 g of toluene were added 26.9 g of bis[tris($\beta,\beta$-dimethylphenethyl)tin] oxide and 8.0 g of o-chlorobenzoic acid. The mixture was worked up in the same way as in Synthesis Example 1, (B) to give 33.4 g (yield 98.3%) of tris($\beta,\beta$-dimethylphenethyl)tin o-chlorobenzoate as a slightly yellow viscous syrup.

Tin content: 16.8% (theory: 17.07%), Refractive index: $n_D^{25}$ 1.5874.

SYNTHESIS EXAMPLE 3

Sodium caprylate 6.6 g was added to 200 ml of isopropanol, and with stirring, the mixture was heated to 50° C. To the resulting solution was added 22.2 g of tris($\beta,\beta$-dimethylphenethyl)tin chloride over 30 minutes. The mixture was further stirred for 30 minutes. The insoluble material precipitated was separated by filtration, and the filtrate was concentrated to give 25.1% (yield 94.8%) of tris($\beta,\beta$-dimethylphenethyl)tin caprylate as a slightly pale yellow viscous syrup.

Tin content: 17.6% (theory: 17.9%), Refractive index: $n_D^{25}$ 1.5462.

In accordance with the procedures given in Synthesis Examples 1 to 3, the compounds of formula (I) shown in Table 1 below were produced. Table 1 also show the compounds produced in Synthesis Examples 1 to 3.

TABLE 1

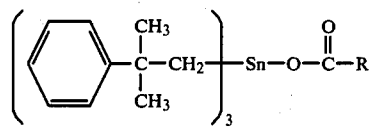

| Compound No. | R | Appearance | Melting point (°C.) or refractive index ($n_D^{25}$) |
| --- | --- | --- | --- |
| 1 | —(CH$_2$)$_6$—CH$_3$ | Slightly pale yellow viscous substance | 1.5462 |
| 2 | —(CH$_2$)$_7$—CH$_3$ | Slightly pale yellow viscous substance | 1.5459 |
| 3 | —(CH$_2$)$_8$—CH$_3$ | Slightly pale yellow viscous substance | 1.5420 |
| 4 | —(CH$_2$)$_{10}$—CH$_3$ | Slightly pale yellow viscous substance | 1.5387 |
| 5 | phenyl | White solid | 74–75 |
| 6 | 4-isopropylphenyl | Yellow viscous substance | 1.5775 |
| 7 | 2-chlorophenyl | Slightly yellow viscous substance | 1.5874 |
| 8 | 2,4-dichlorophenyl | Pale red viscous substance | 1.5921 |
| 9 | 3-chlorophenyl | Slightly pale yellow viscous substance | 1.5879 |
| 10 | 2,5-dichlorophenyl | Slightly pale yellow viscous substance | 1.5897 |
| 11 | 4-bromo-2-(dimethyl)phenyl (with CH$_3$–C–CH$_3$ substituent) | Dark red viscous substance | 1.6851 |
| 12 | 4-chloro-2-(dimethyl)phenyl (with CH$_3$–C–CH$_3$ substituent) | Red viscous substance | 1.5746 |

FORMULATION EXAMPLE 1

Dust:

Five parts by weight of compound No. 1, 94.7 parts by weight of clay and 0.3 part by weight of isopropyl phosphate are mixed and pulverized to form a dust. It can be applied as such by spraying.

FORMULATION EXAMPLE 2

Fine dust:

Fifteen parts by weight of compound No. 3, 10 parts by weight of white carbon and 75 parts by weight of fine clay powder are mixed and pulverized to form a fine dust. It can be applied as such by spraying.

FORMULATION EXAMPLE 3

Fifty parts by weight of compound No. 4, 40.5 parts by weight of diatomaceous earth, 5 parts by weight of white carbon, 3 parts by weight of polyoxyalkylene alkylaryl ether sulfate and 1.5 parts by weight of alkylbenzenesulfonate salt are mixed and pulverized to form a wettable powder. It can be sprayed after suspending it in water.

FORMULATION EXAMPLE 4

Emulsifiable concentrate:

Twenty-five parts by weight of compound No. 7, 3 parts by weight of alkylaryl sulfonate, 10 parts of polyoxyalkylene alkylaryl ether and 62 parts by weight of xylene were uniformly dissolved to form an emulsifiable concentration. It can be sprayed after diluting it with water.

TEST EXAMPLE 1

Test for efficacy on two-spotted spider mites (*Tetranychus urticae*):

Ten spider mite imagoes were inoculated onto mottled kidney bean plants (two main leaves) grown in pots. After the mites settled, a wettable powder prepared in accordance with Formulation Example 3 was diluted with water to a predetermined concentration and the main leaves were dipped for 10 seconds in the diluted chemical. The leaves were then left to stand in a constant-temperature chamber kept at 25° C. Twenty-four hours later, the number of dead mites was examined, and the kill ratio was calculated. The results are shown in Table 2.

TABLE 2

| Compound No. | Kill ratio (%) | | | |
|---|---|---|---|---|
| | 500 ppm | 250 ppm | 125 ppm | 62.5 ppm |
| 1 | 100.0 | 100.0 | 100.0 | 86.7 |
| 2 | 100.0 | 100.0 | 100.0 | 60.0 |
| 3 | 100.0 | 100.0 | 100.0 | 83.3 |
| 4 | 100.0 | 100.0 | 100.0 | 98.0 |
| 5 | 78.4 | — | — | — |
| 6 | 100.0 | 100.0 | 30.0 | 0 |
| 7 | 100.0 | 100.0 | 100.0 | 80.0 |
| 8 | 100.0 | 100.0 | 100.0 | 73.3 |
| 9 | 75.8 | — | — | — |
| 10 | 75.8 | — | — | — |
| 11 | 100.0 | 100.0 | 86.7 | 33.3 |
| 12 | 100.0 | 92.6 | 50.0 | 0 |
| Comparative chemical | | | | |
| 1* | 100.0 | 100.0 | 61.7 | 13.3 |
| 2** | 100.0 | 100.0 | 100.0 | 76.7 |
| 3*** | 85.4 | — | — | — |

TABLE 2-continued

| Compound No. | Kill ratio (%) | | | |
|---|---|---|---|---|
| | 500 ppm | 250 ppm | 125 ppm | 62.5 ppm |
| Non-treated | 0 | 0 | 0 | 0 |

Comparative chemical 1: bis[tris-$\beta,\beta$-dimethyl phenethyl)tin]oxide $$\left[\left(\left\langle\bigcirc\right\rangle-\underset{CH_3}{\overset{CH_3}{\underset{|}{C}}}-CH_2\right)_3-Sn\right]_2 O$$

Comparative chemical 2: tricyclohexyltin hydroxide $$\left(\left\langle H\bigcirc\right\rangle\right)_3-Sn-OH$$

Comparative chemical 3: tris($\beta,\beta$-dimethylphenethyl)-tin acetate $$\left(\left\langle\bigcirc\right\rangle-\underset{CH_3}{\overset{CH_3}{\underset{|}{C}}}-CH_2\right)_3-Sn-O-\overset{O}{\overset{\|}{C}}-CH_3$$

TEST EXAMPLE 2

Test for efficacy on *Tetranychus kanzawai*:

Ten mite imagoes were inoculated onto mottled kidney bean plants (two main leaves) grown in pots. After the mites settled, an emulsifiable concentrate prepared in accordance with Formulation Example 4 was diluted with water to a predetermined concentration and the main leaves were dipped for 10 seconds in the diluted chemical. The leaves were then left to stand in a constant-temperature chamber kept at 25° C. Twenty-four hours later, the number of dead mites was examined, and the kill ratio was calculated. The results are shown in Table 2.

Comparative chemicals 1, 2 and 3 were the same as the comparative chemicals used in Test Example 1.

TABLE 3

| Compound No. | Kill ratio (%) | |
|---|---|---|
| | 100 ppm | 50 ppm |
| 1 | 100.0 | 100.0 |
| 2 | 100.0 | 100.0 |
| 3 | 100.0 | 100.0 |
| 4 | 100.0 | 100.0 |
| 5 | 86.7 | 30.0 |
| 6 | 100.0 | 93.3 |
| 7 | 100.0 | 100.0 |
| 8 | 100.0 | 100.0 |
| 9 | 76.7 | 30.0 |
| 10 | 56.7 | 3.3 |
| 11 | 100.0 | 100.0 |
| 12 | 100.0 | 100.0 |
| Comparative chemical | | |
| 1 | 95.0 | 46.7 |
| 2 | 100.0 | 86.7 |
| 3 | 50.0 | 23.3 |
| Non-treated | 0 | 0 |

TEST EXAMPLE 3

Test for efficacy on citrus red mites (*Panonychus citri*):

A wettable powder prepared in accordance with Formulation Example 3 was diluted with water to a concentration of 125 ppm to prepare a test chemical. The chemical was sprayed fully onto the leaves (on which the citrus red mites were parasitic) of an orange tree (5 years old) grown in pots. The number of surviving larvae and imagoes of the mites were examined before the spraying and 4 days, 10 days, 20 days and 30 days after the spraying. The control efficiency was calculated in accordance with the following equation, and the results are shown in Table 4.

Comparative chemicals 1, 2 and 3 were the same as the comparative chemicals used in Test Example 1.

$$\text{Control efficiency} = \left(1 - \frac{\Sigma Tai/Tb}{\Sigma Cai/Cb}\right) \times 100$$

ΣTai: the total number of the surviving larvae and imagoes examined after the spraying in the treated area (excluding that examined 4 days later)
Tb: the number of larvae and imagoes before the spraying in the treated area
ΣCai: the total number of the surviving larvae and imagoes examined after the spraying in the non-treated area (excluding that examined 4 days later)
Cb: the number of larvae and imagoes before the spraying in the non-treated area

TABLE 4

| Compound No. | Concentration of the chemical (ppm) | Number of the imagoes and larvae per 2.5 leaves | | | | | Control efficiency |
|---|---|---|---|---|---|---|---|
| | | Before spraying | 4 days after | 10 days after | 20 days after | 30 days after | |
| 1 | 125 | 46 | 1 | 0 | 0 | 0 | 100 |
| 2 | " | 82 | 1 | 1 | 0 | 0 | 100 |
| 3 | " | 35 | 0 | 0 | 0 | 0 | 100 |
| 4 | " | 41 | 0 | 0 | 0 | 0 | 100 |
| 6 | " | 36 | 2 | 1 | 0 | 0 | 99 |
| 11 | " | 48 | 3 | 1 | 0 | 0 | 99 |
| Comparative chemical | | | | | | | |
| 1 | 125 | 41 | 3 | 2 | 0 | 0 | 98 |
| 2 | " | 28 | 2 | 0 | 0 | 0 | 100 |
| 3 | " | 35 | 16 | 29 | 14 | 21 | 57 |
| Non-treated | — | 30 | 27 | 33 | 36 | 27 | — |

TEST EXAMPLE 4

Test for phytotoxicity on fruit trees and vegetables:
A phytotoxicity test was carried out on pear ("20th century", 15 years old), peach ("hakuto", 15 years old), apple ("star king", 4 years old), water melon ("shimatama"), cucumber ("shinko A") and eggplant ("senryo nigo") grown in fields and orange ("unshu", 5 years old) grown in a pot. A wettable powder prepared in accordance with Formulation Example 3 was diluted to 500 ppm with water. The resulting diluted chemical was fully sprayed by a small-sized hand sprayer to the point of run-off from the leaves. The same chemical was sprayed onto five main leaves of vegetables. Seven days after the spraying, the plants were examined for phytotoxicity. The results are shown in Table 5 by the following phytotoxicity rating.
—: No injury
+: Slight injury
++: Medium injury
+++: The plants were about to wither.

TABLE 5

| Compound No. | Pear | Peach | Orange | Apple | Water melon | Cucumber | Eggplants |
|---|---|---|---|---|---|---|---|
| 1 | — | — | — | — | — | — | — |
| 2 | — | — | — | — | — | — | — |
| 3 | — | — | — | — | — | — | — |
| 4 | — | — | — | — | — | — | — |
| 6 | — | — | — | — | — | — | — |
| 7 | — | — | — | — | — | — | — |
| 8 | — | — | — | — | — | — | — |
| 11 | — | — | — | — | — | — | — |
| 12 | — | — | — | — | — | — | — |
| Comparative chemical | | | | | | | |
| 1 | — | — | — | — | — | — | — |
| 2 | — | — | — | — | +++ | ++ | + |
| 3 | — | — | — | — | — | — | — |
| Non-treated | — | — | — | — | — | — | — |

What is claimed is:
1. A compound represented by the formula

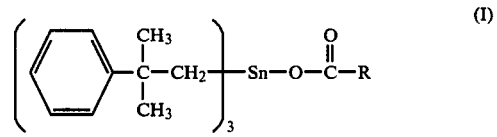

wherein R represents an alkyl group having 7 to 11 carbon atoms, a phenyl group which is substituted by 3-isopropyl, 2-chloro or 2,4-dichloro, or a group of the formula

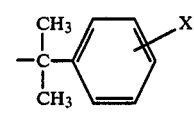

in which X represents a chlorine or bromine.
2. A compound of claim 1 wherein R is —$C_{11}H_{23}$.
3. A miticide composition comprising as an active ingredient a miticidally effective amount of a compound of the formula

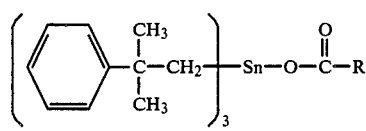
(I)

wherein R represents an alkyl group having 7 to 11 carbon atoms, a phenyl group which is substituted by 3-isopropyl, 2-chloro or 2,4-dichloro or a group of the formula

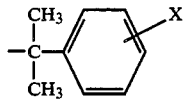

in which X represents a chlorine or bromine atom, and an agriculturally acceptable carrier or diluent therefor.

4. A composition of claim 3 wherein R is $C_{11}H_{23}$.

5. A method of combating mites which comprises applying a miticidally effective dosage of a compound represented by the formula

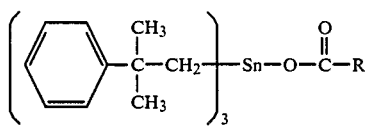
(I)

wherein R represents an alkyl group having 7 to 11 carbon atoms, a phenyl group which is substituted by 3-isopropyl, 2-chloro or 2,4-dichloro or a group of the formula

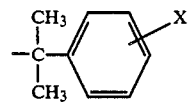

in which X represents a chlorine or bromine atom, onto mites or their habitat.

6. A method of claim 5 wherein R is $-C_{11}H_{23}$.

* * * * *